United States Patent [19]
Iversen et al.

[11] Patent Number: 4,541,421
[45] Date of Patent: Sep. 17, 1985

[54] HALO FIXATION SYSTEM

[75] Inventors: Alfred A. Iversen; William J. Eastman, both of Hopkins, Minn.

[73] Assignee: PMT, Inc., Hopkins, Minn.

[21] Appl. No.: 596,392

[22] Filed: Apr. 3, 1984

[51] Int. Cl.$^4$ .............................................. A61H 1/02
[52] U.S. Cl. ................................................. 128/87 B
[58] Field of Search ................... 128/69, 75, 76, 89 R, 128/89 A, 87 B, 87 R, 92 A, 92 R

[56] References Cited

U.S. PATENT DOCUMENTS

| | | | |
|---|---|---|---|
| 3,336,922 | 8/1967 | Taylor | 128/75 |
| 3,957,040 | 5/1976 | Calabrese | 128/75 |
| 4,127,119 | 11/1978 | Kronner | 128/92 A |
| 4,194,501 | 3/1980 | Watt | 128/87 B |
| 4,312,336 | 1/1982 | Danieletto et al. | 128/92 A |

Primary Examiner—John D. Yasko
Assistant Examiner—Christa K. Scott
Attorney, Agent, or Firm—Hugh D. Jaeger

[57] ABSTRACT

Halo fixation system for fixation of a head about an orthopedic jacket with an attached halo assembly with respect to the cervical region such as for spine trauma. The halo fixation system includes eight fixated round ball-socket and rod assemblies, four assemblies affixed to the jacket and four assemblies in twin opposing captured elevation screw assemblies. The halo is adjustable through the twin captured elevation screw assemblies. Rods connected between the ball and socket assemblies of the jacket and of the captured elevation assemblies which support the halo. The halo can be either metal or composite material, and either a closed or open halo. The halo is omni adjustable about the head based on the omni directional adjustable rod in the ball-socket configurations located about the halo head piece and the jacket.

10 Claims, 7 Drawing Figures

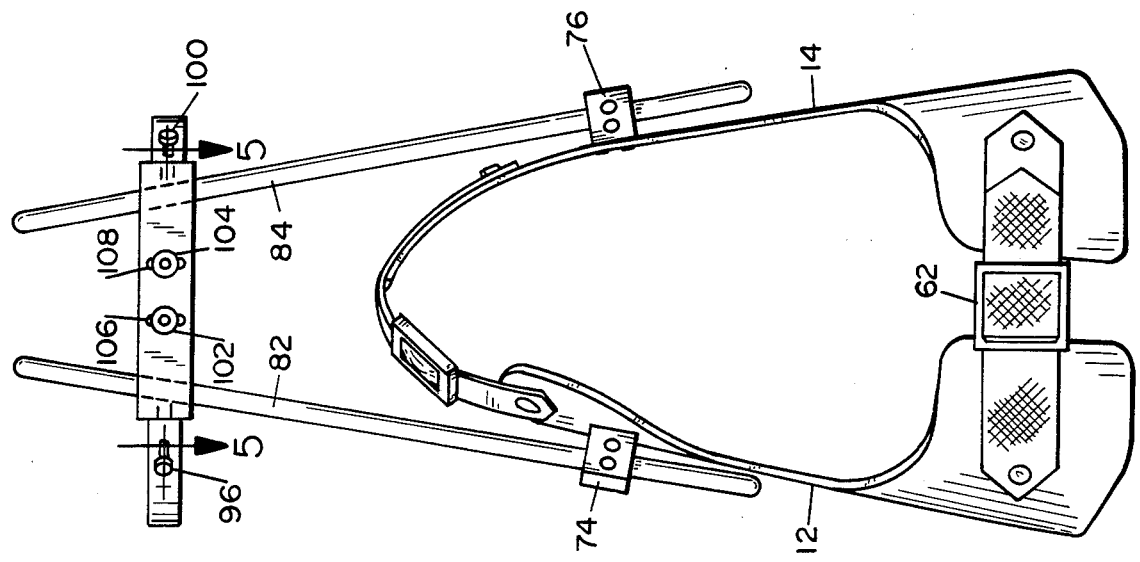
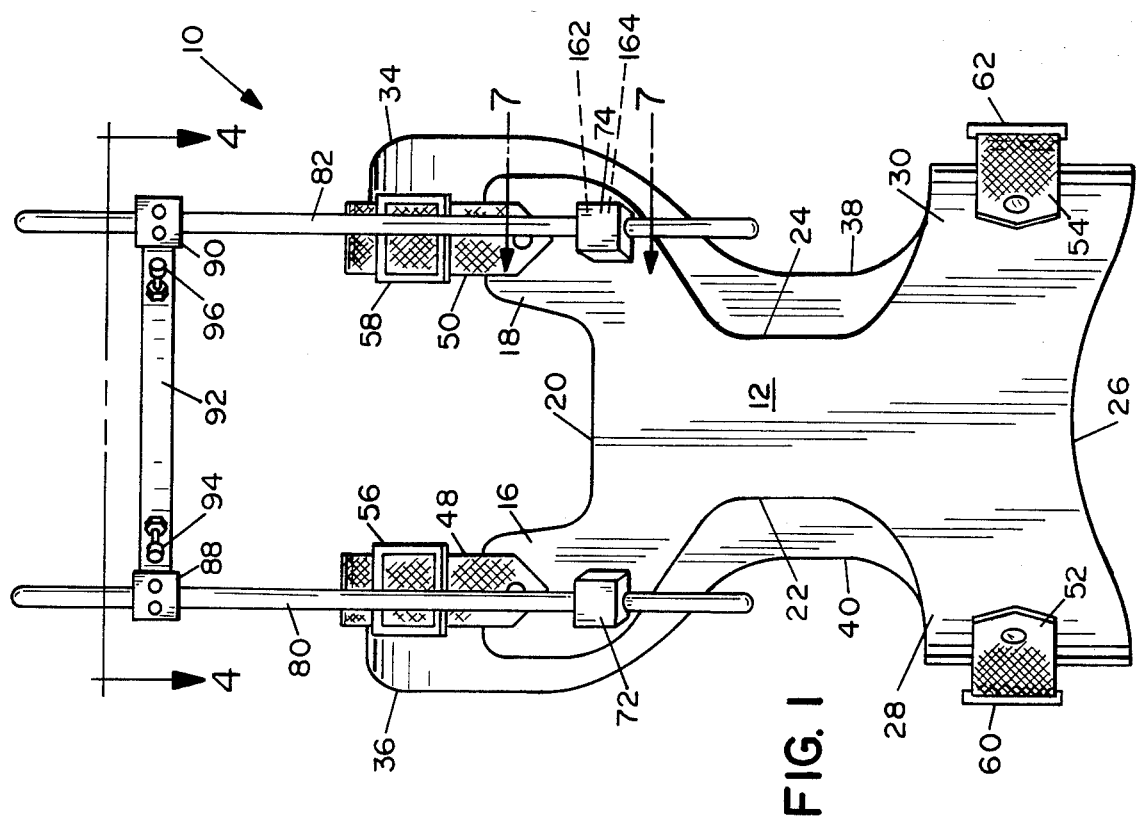
FIG. 1
FIG. 2

HALO FIXATION SYSTEM

BACKGROUND OF THE INVENTION

1. Field of the Invention

The present invention pertains to a surgical appliance, and more particularly pertains to a halo fixation system as an orthotic or orthopedic brace following surgery or accidents where there is trauma to the spine.

2. Description of the Prior Art

Prior art halos for cervical traction include extensive metal super structure, numerous rods, and numerous nut and bolt assemblies. Some of the prior art systems were as complicated as a basic erector set super structure and also resembled older style chemistry clamp assemblies of bars and rods.

More importantly, the prior art clamp type mechanisms and equipment consisted of metal hardware, including metal bars, metal pins, and metal clamps which did not provide the X-ray compatibility of the patient.

Also, the prior art halos were prone to severe loosening of the hardware during the patient's ambulatory periods. Further, the prior art systems provided that there were considerable and extensive adjustments of hardware required of the nuts and bolts to obtain the desired placement. It was even harder for the patient, in the prior art systems, to maintain any type of hygiene care wearing a halo vest.

The present invention overcomes the disadvantages of the prior art by providing a halo fixation system composed of composite materials, the materials being light weight, and incorporating new and novel capturing assemblies providing for complete tilt-angulation-elevation adjustments, providing for a secure orthotic attachment.

SUMMARY OF THE INVENTION

The general purpose of the present invention is to provide a halo fixation system for fixation of the cervical neck region following trauma to the spine, the components being of a light weight material and secured through a ball, rod, and screw assembly which allows for complete tilt-angulation and elevation adjustments to the neck. The halo fixation system, more importantly, provides for X-rays compatibility, or the like, while the patient is wearing the system, and also allows for freedom of movement through ball rod assemblies. A low profile above the patient's head is maintained, as well as a low body profile of the device about the patient's body.

According to one embodiment of the present invention, there is provided a halo fixation system for a patient including a front and rear jacket for conforming to the body, straps and locking buckles for adjustable securing the jackets together about the patient's waist, a plurality of ball and socket assemblies secured to upper portions of each should flange of the jacket, rods adjustably secured therein, twin captured elevation screw assemblies adjustably including ball and socket assemblies secured to upper portions of the rods, a halo secured to the twin captured elevation screw assemblies with bolt assemblies, the twin captured elevation screw assemblies including slots with adjustable screws therein for adjusting the elevation of the halo with respect to the bolt assemblies whereby the tilt-angulation-elevation adjustments to the halo are provided through the interaction of the rods with respect to the ball and socket assemblies, and the slotted adjustments in the twin captured elevation screw assemblies.

One significant aspect and feature of the present invention is that the halo fixation system provides omni directional adjustment through vertical bar assemblies through a captured ball, as well as elevation and tilt adjustment through captured screw assemblies.

Another significant aspect and feature of the present invention is a halo fixation system which provides for computer-tomography (CT) compatibility, nuclear magnetic residence (NMR) compatibility, and X-ray compatibility, especially in the cervical area.

A further significant aspect and feature is that the halo fixation system is light weight.

An additional significant aspect and feature of the present invention is that the ease of assembly and attachment to the patient along with security of attachment.

Having thus described the embodiments of the present invention, it is the principal object hereof to provide a halo fixation system.

One object of the present invention is to provide a omni directional tilt-angulation-elevational adjustment to the halo with respect to the patient.

Another object of the present invention is to provide a halo fixation system which is easily utilized by medical personnel not requiring complex mechanical adjustments or the like.

A further object of the present invention is a halo fixation system which is low cost and disposable providing for one time usage.

An additional object is that the present invention provides a low profile about the patient's head.

BRIEF DESCRIPTION OF THE DRAWINGS

FIG. 1 illustrates a front view of a halo fixation system, the present invention;

FIG. 2 illustrates a side view;

DESCRIPTION OF THE PREFERRED EMBODIMENTS

Figure 3:
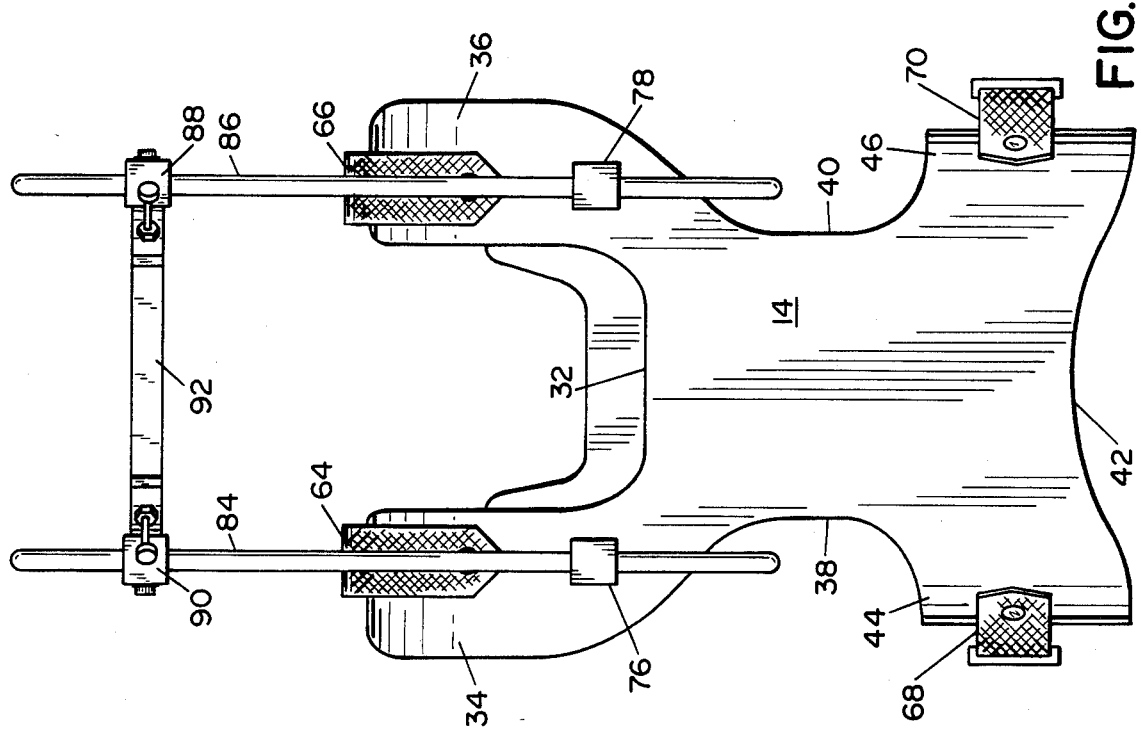
FIG. 3 illustrates a back view.

FIG. 1 illustrates a front view of a halo fixation system 10, the present invention, including a front jacket 12 and a back jacket 14, the jackets of polyethylene. The front jacket 12 includes upper flanges 16 and 18, a neck indentation 20, a breast indentation 22 and 24, and a stomach indentation 26. The sides 28 and 30 are curved for conforming around the waist. Likewise, the back jacket 14, as illustrated in FIG. 3, also includes a neck indentation 32, upper flanges 34 and 36, back indentations 38 and 40, buttocks indentation 42, and curved sides 44 and 46. The front and back jackets 12 and 14, respectively, can be formed from a polyethylene material through heat methods to conform to the surfaces of an individual body and also provides for flexibility to conform to the surfaces of an individual's body.

Straps 48, 50, 52, and 54 along with mating male and female buckles, such as Fastek buckles, 56, 58, 60, and 62, or the like, secure to the corresponding straps 64, 66, 68, and 70 as illustrated in FIG. 3. The straps can be the typical nylon seat belt webbing strap, or the like, and are secured with nut and bolt assemblies to the waist positions on the jacket as illustrated.

Figure 4:
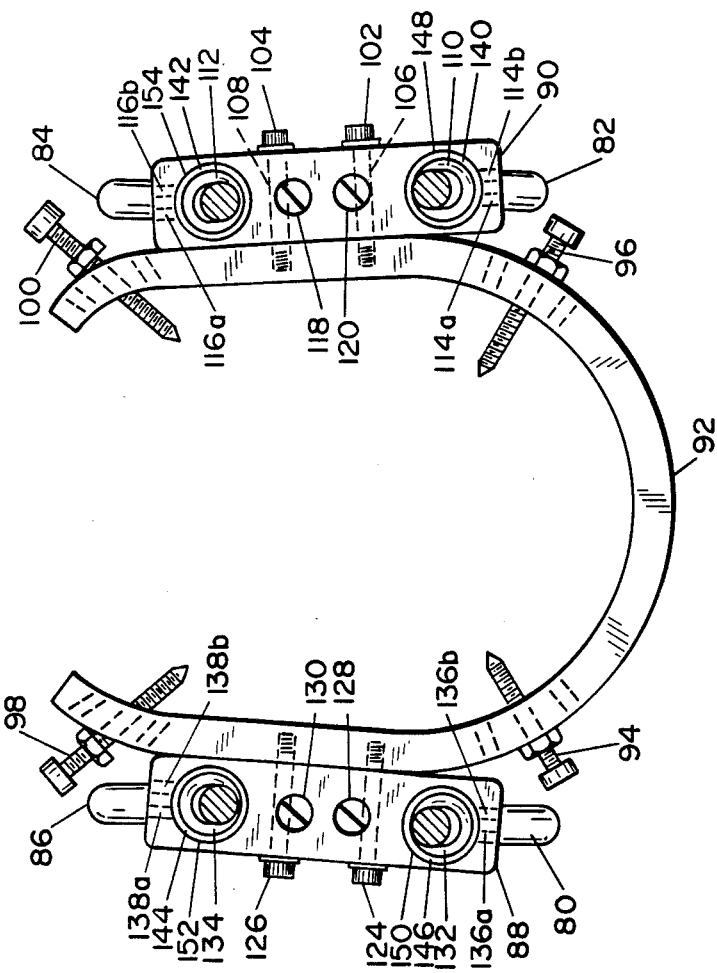
FIG. 4 illustrates a top view taken along line 4—4 of FIG. 1.
Figure 6:
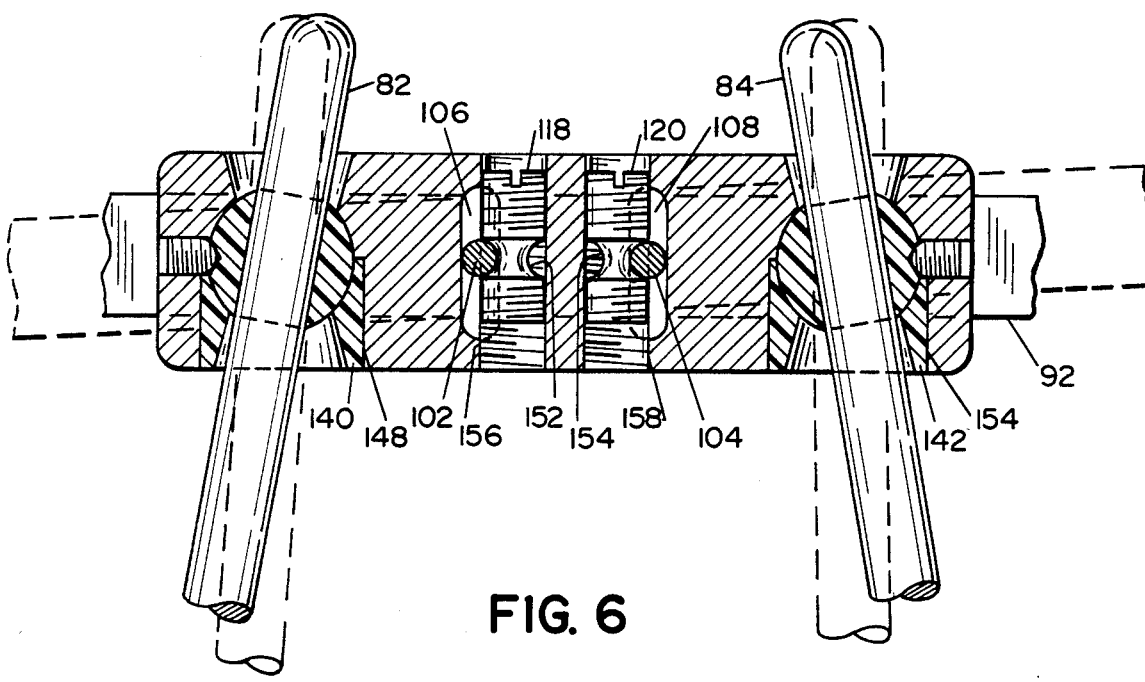
FIG. 6 illustrates a view taken along line 6—6 of FIG. 5.
Figure 7:
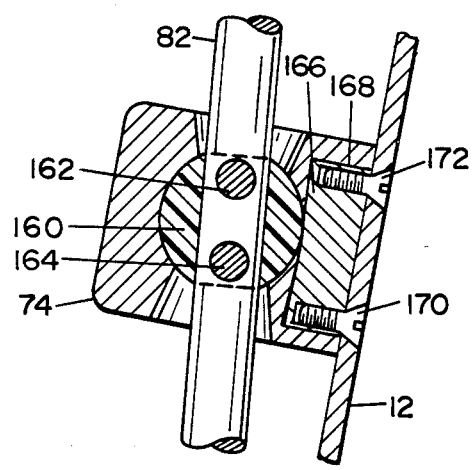
FIG. 7 illustrates a view taken along line 7—7 of FIG. 1.

Four round ball-socket assemblies 72 and 74 in FIG. 1, and 76 and 78 in FIG. 3, screw to the jacket assembly as illustrated in FIG. 7 as later described and include vertically aligned allen head set screws for securing the ball which secures the rod in position as illustrated in FIG. 7 and later described in detail. Rods 80 and 82 in FIG. 1 and 84 and 86 in FIG. 3 secure to the assemblies 72-78. The rods also secure to twin captured elevation screw assemblies 88 and 90 as illustrated in particular detail in FIGS. 5 and 6. A halo 92 secures to the assemblies 88 and 90 as illustrated in FIG. 4 and also FIGS. 5 and 6. In this particular example, the halo 92 is an open halo as illustrated in FIG. 4, and includes four skull pins 94, 96, 98, and 100, as also illustrated in FIG. 4. The halo 92 can be made of a composite material such as acetal resin, also known as Delrin. This material also forms the blocks for the round ball-rod assemblies and the twin captured elevation screw assemblies. The rods can be carbon graphite rods with a fiberglass internal composition or other suitable materials.

FIG. 2 illustrates a side view of the halo fixation system 10 where all numerals correspond to those elements previously described. Particularly illustrated is the twin captured elevation screw assembly, including side screws 102 and 104 and corresponding slots 106 and 108. The operation is later described in detail in FIG. 5. All other numerals correspond to those elements previously described. Particularly noted is the assembly 74 illustrating the side position relationship of the set screws, which is later described in detail in FIG. 7.

FIG. 3 illustrates a back view where all numerals correspond to those elements previously described. The opposing symmetry is noted between the front of FIG. 1 and this figure.

Figure 5:
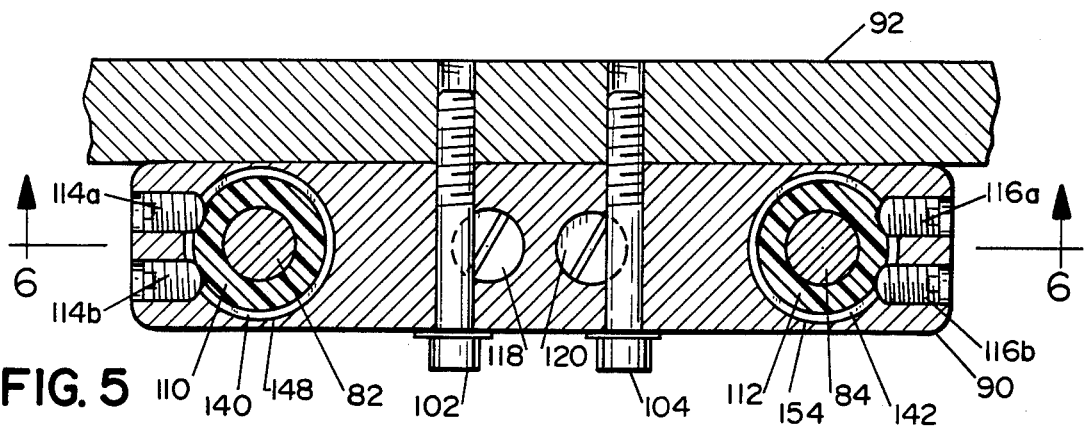
FIG. 5 illustrates a view taken along line 5—5 of FIG. 2.

FIG. 4 illustrates a view taken along line 4—4 of FIG. 1. With reference to the elevation assembly 90, balls 110 and 112 are illustrated, corresponding set screws 114a and 114b and 116a and 116b, and screws 102 and 104 are also illustrated. Elevational halo fixation screws 118 and 120 are illustrated with operation later described in detail in FIG. 6. Like components are illustrated for elevation assembly 88 including screws 124 and 126, elevational screws 128 and 130, balls 132 and 134, and set screws 136a and 136b and 138a and 138b. Round configured members 140-146 are secured into holes 148-154 for securing the balls within the respective sockets as also illustrated in FIGS. 5 and 6. These members 140-146 can be secured, such as through glue or the like, or can be of a press fit or locking snap relationship.

FIG. 5 illustrates a view taken along line 5—5 of FIG. 2 where all numerals correspond to those elements previously described. Particularly illustrated is the relationship of the cap screws 102 and 104 to the halo 92 securing the assembly 90 thereto, and the elevational screws 118 and 120 as illustrated in FIG. 6.

FIG. 6 illustrates a view taken along line 6—6 of FIG. 5 where all numerals correspond to those elements previously described. Particularly illustrated is the relationship of the slots 106 and 108 with respect to the cap screws 102 and 104. More so, the elevational screws 118 and 120 include grooves 152 and 154 which provide for elevational adjustment with respect to the cap screws 102 and 104. The threaded holes 156 and 158 provide for the elevational adjustment of the screws 118 and 120 which likewise carry the cap screws 102 and 104 in the halo assembly 90 secured thereto. Member 140 and 142 are illustrated for securing the balls into the respective sockets.

FIG. 7 illustrates a sectional view taken along line 7—7 of FIG. 1 of a ball and socket assembly 74. This assembly, as represented, includes a ball 160, set screws 162 and 164 as illustrated in FIG. 1, a disk 166 secured into a corresponding hole 168, and four screws two of which are shown 170 and 172 which secure the hole assembly 74 including the disk 166 to the jacket portion 12. Likewise, this assembly is utilized on each shoulder flange of the jacket.

MODE OF OPERATION

The halo fixation system can be immediately applied to a patient in the emergency room. The patient can then be moved without danger of dislocation of a cervical injury. Neurologically sound patients can ambulate and return to a semblance of normal existence within a few days, while long hospital stays are eliminated. While the halo system 10 has been illustrated with an open halo 92, likewise, a closed halo can be utilized within the scope of the present invention. The halo fixation system of the present invention due to the use of composite components and space age technology components, provides that there is minimum weight about the patient and no weight of any significance placed on the neck-shoulder-muscle group, as well as maintaining a low device profile about the body. There are extra holes provided in the halo ring 92 as illustrated in FIG. 4 by dashed lines for the skull pins for engagement in these threaded holes and secured thereto by nuts 94a-100a. By adjusting the position of the infinitely adjustable rods 80-86, the profile of the halo is such that the majority of the length of the rod can extend all of the way from the halo ring down beyond the socket assemblies 72-76, thus eliminating any cumbersome or unsightly profile extending above patient's head. The ball rods allow three degrees of movement in three axis of movement thus providing a nominal amount of give and flex between the patient and the halo fixation system. This makes the halo fixation system acceptable to the individual patient.

The halo fixation system can be secured to the patient when the patient is in a horizontal position or a vertical position, and preferably would be attached after the halo ring 92 is secured to the skull of the patient. The medical personnel decides whether there is traction on the patient during the fixation procedure and such is allowed for with the halo ring. The adjustment can usually be provided for once the jacket and graphite rods are in position between the ball assemblies affixed to the jacket and the twin captured elevation screw assemblies. The rods are slid into position, adjusted accordingly, and all screws affixing the balls, as well as the elevation screws and bolts securing the elevation assemblies to the halo ring, are adjusted and secured with the allen wrench fittings. It is noted for convenience that all of the securing bolts are allen head bolts with the exception of the skull bolts which requires a wrench to secure the locking nuts.

Minor elevational adjustment of up to three degrees of tilt and one inch of elevation can be provided by the elevational screws 118 and 120 and likewise 128 and 130 providing for movement of the corresponding bolts within the slots while riding within the grooves of the elevational screws.

A liner is provided on the interiors of the vest, where the liner can be changed by unstrapping the vest with the patient in a horizontal position and pulling the liner, which can be secured to the inside of the front and back jackets with velcro or the like. The liner can be a combined cotton-polyester material or sheep skin or cordel and secured with velcro. This provides for hygiene of the patient.

We claim:

1. Halo fixation system for a patient comprising:
   a. front and back opposing jackets configured to conform to the front and back surfaces of a patient's body, and a plurality of adjustable straps and locking buckles in between for securing said front and back jacket together;
   b. ball and socket means secured to upper areas of said front and back jackets;
   c. rods extending through each of said ball and socket means upwardly, a ball for each ball and socket means surrounding each of said rods in a free-floating relationship;
   d. elevational assembly means including ball and socket means at each end, each of said ball and socket means secured to each of said rods, a ball for each of said ball and socket means surrounding each of said rods in a free-floating relationship; and,
   e. halo ring secured to each of said elevational assembly means, said halo including a plurality of skull pins for securing to a patient's skull.

2. System of claim 1 comprising slots in said elevational assembly means, and elevational adjusting screws for adjusting bolts securing said elevational assembly means to said halo means for adjusting elevation, tilt, and traction.

3. System of claim 1 wherein said ball and socket means, rods, elevational assembly means, and halo of composite materials.

4. System of claim 1 wherein said halo has an infinite adjustability range with respect to said front and back jacket.

5. System of claim 1 wherein said halo is open.

6. System of claim 1 wherein said halo is closed.

7. System of claim 1 wherein said halo is metal.

8. System of claim 1 wherein said halo is composite.

9. System of claim 1 including two allen head bolts securing each ball in said socket means.

10. Halo fixation system comprising:
    a. front and back opposing jacket halves configured for conforming to front and back surfaces of an individual's body, and a plurality of adjustable straps and locking buckles secured between sides and top of said front and back jacket halves;
    b. free-floating ball and socket means secured to opposing upper areas of each of said front and back jackets;
    c. longitudinal rods extending through each of said free-floating balls and means for securing each of said rods within said free-floating ball and socket means;
    d. elevational assembly means including free-floating ball and socket means at each end of said elevational assembly means, each of said free-floating ball and socket means in said elevational assembly means secured to another end of said rods by securing means, two substantially vertical slots in each of said opposing elevational assembly means, and elevational adjusting screws in each of said slots; and,
    e. halo ring secured to each of said elevational assembly means by bolts extending through said halo ring and into each of said vertical slots, and screws positioned in each of said vertical slots for adjusting said halo ring about said elevational assembly means for elevational tilt and traction of an individual's skull.

* * * * *